United States Patent [19]

Magyar et al.

[11] Patent Number: 5,120,711
[45] Date of Patent: Jun. 9, 1992

[54] SYNERGISTICALLY ACTIVE VETERINARY COMPOSITIONS AND PROCESS FOR PREPARING SAME

[75] Inventors: Károly Magyar; Ferenc Simon; János Varga; Attila Nagy; László Puskás; Pál Fekete; János Egri; Katalin Zukovics, all of Budapest, Hungary

[73] Assignee: EGIS Gyogyszergyar, Budapest, Hungary

[21] Appl. No.: 616,813

[22] Filed: Nov. 20, 1990

Related U.S. Application Data

[63] Continuation of Ser. No. 331,391, Mar. 31, 1989, abandoned.

[30] Foreign Application Priority Data

Apr. 1, 1988 [HU] Hungary .............................. 1606/88

[51] Int. Cl.$^5$ ...................... A61K 31/47; A61K 37/00
[52] U.S. Cl. ........................................ 514/11; 514/311
[58] Field of Search ................................... 514/11, 311

[56] References Cited

U.S. PATENT DOCUMENTS

| | | | |
|---|---|---|---|
| 2,695,881 | 11/1954 | Elliot et al. | 514/311 |
| 3,929,989 | 12/1975 | Bergt | 514/152 |
| 3,980,778 | 9/1976 | Ayer et al. | 514/171 |
| 4,011,312 | 3/1977 | Reuter et al. | 424/115 |
| 4,018,918 | 4/1977 | Ayer et al. | 514/171 |
| 4,166,118 | 8/1979 | Cosgrove et al. | 514/311 |
| 4,376,787 | 3/1983 | Lentsch et al. | 514/576 |
| 4,600,711 | 7/1986 | Swerczek | 514/23 |
| 4,650,790 | 3/1987 | Simon et al. | 514/35 |

OTHER PUBLICATIONS

Ernest Javetz M.D. Ph.D., *Polymyxin, Neomycin, Bacitracin* copyright 1956 pp. 14, 18.

*Primary Examiner*—Frederick E. Waddell
*Assistant Examiner*—Kevin E. Weddington
*Attorney, Agent, or Firm*—Keil & Weinkauf

[57] ABSTRACT

The invention relates to synergistically active veterinary compositions useful particularly for the treatment of mastitis and metritis. The invention further relates to a process for preparing these compositions. The compositions according to the invention comprise, based on 1 part by weight of 6,9,18-tris(2-aminoethyl)-15-benzyl-21-[−2,8-bis(2-aminoethyl)-5-(1-hydroxyethyl)-15-methyl-4,7,10-trioxo-3,6,9-triazaheptadecanamido]-3-(1-hydroxyethyl)-12-isobutyl-1,4,7,10,13,16,19-heptaazacyclotricosane-2, 5,8,11,14,17,20-heptaone or a pharmaceutically acceptable acid addition salt thereof, 1 to 1000 parts by weight of 1-(2-chlorophenyl)-diphenylmethyl-1H-imidazole or 1 to 400 parts by weight of 2-methyl-5,7-dichloro-8-hydroxyquinoline, respectively, optionally in admixture with carriers and/or additives commonly used in the pharmaceutical industry.

2 Claims, No Drawings

SYNERGISTICALLY ACTIVE VETERINARY COMPOSITIONS AND PROCESS FOR PREPARING SAME

This application is a continuation of application Ser. No. 07.331,391, filed on Mar. 31, 1989, now abandoned.

The invention relates to synergistically active veterinary compositions, useful particularly for the treatment of mastitis and metritis. The invention further relates to a process for preparing these compositions.

The mastitis and metritis of various animal species can cause severe economical losses. This inflammation process, induced by various bacteria, is accompanied by e.g. a significant decrease in the milk production and number of progeny of cattle.

At present, various antibacterial agents are employed for the treatment of mastitis and metritis, which is usually carried out topically. Although the infection in itself is caused by bacteria, a fungal infection frequently occurs during the treatment, therefore a really favourable result can be ensured only by a veterinary composition equally effective against gram-positive and gram-negative bacteria as well as against fungi.

In the practice, the treatment is carried out in the most cases by using antibiotics.

A suspension of 6,9,18-tris(2-aminoethyl)-15-benzyl-21-[2,8-bis(2-aminoethyl)-5-(1-hydroxyethyl)-15-methyl-4,7,10-trioxo-3,6,9-triazaheptadecanamido]-3-(1-hydroxyethyl)-12-isobutyl-1,4,7,10,13,16,19-heptaazacyclotricosane-2,5,8,11,14,17,20-heptaone (polymyxin B) and 4-dimethylamino-3,5,6,10,12,12a-hexahydroxy-6-methyl-1,11-dioxo-1,4,4a,5,5a,6,11,12a-octahydronaphthacene-2carboxamide (oxytetracycline) is used for the treatment of both mastitis and metritis; however, this composition exerts a very weak effect on several bacterial species (e.g. *Staphylococcus aureus* or *Streptococcus zooepidermicus*).

A combination of 2,4-diamino-5-(2,6-diamino-2,6-dideoxy-$\beta$-D-glucosyloxy)-6-[3-0-(2,6-diamino-2,6-dideoxy-$\beta$-L-idosyl)-$\alpha$-D-ribosyloxy]-(1R, 2S, 4R, 5S, 6S)-1-cyclohexanol (neomycin) with oxytetracycline is used in a form of an uterine rod or udder infusion. However, these known compositions exert a very weak action on gram-negative bacteria.

A disadvantage of an uterine rod containing 3-[(5-nitrofurfurylidene)amino]-2-oxazolidinone (furazolidone) used for the treatment of metritis consists in that the active ingredient is toxic.

D-(-)-threo-2,2-dichloro-N-[2-hydroxy-1-hydroxymethyl-2-(4-nitrophenyl)ethyl]acetamide (chloramphenicol) alone or together with $N^1$-(4,6-dimethylpyrimidinyl)sulfanylamide (sulfadimidine) is also used for the treatment of metritis in the form of a foam or uterine capsule. However, these compositions are not favourable because they have practically no action on gram-negative bacteria.

6-[4-Dimethylamino-3-hydroxy-6-methyl-2-tetrahydropyranyloxy]-14-ethyl-7,12,13-trihydroxy-4-(5-hydroxy-4-methoxy-4,6-dimethyl-2-tetrahydropyranyloxy)-3,5,7,9,11,13-hexamethyl-1-oxa-2,10-tetradecanedione (erythromycin) is used as udder infusion for the treatment of mastitis. This known composition does not exert any effect on gram-negative bacteria, either.

An udder infusion containing 6-phenylacetylamino-3,3-dimethyl-7-oxo-4-thia-1-azabicyclo[3.2.0]heptane-2-carboxylic acid (benzylpenicillin) together with 3,5-diguanidino-6-[2-0-(2-methylamino-2-deoxy-$\alpha$-N-glucosyl)-$\alpha$-L-streptosyloxy]-1,2,4-cyclohexanetriol sulfate (streptomycin sulfate) is also used which, however, acts only on some bacteria (such as Streptococcus and Staphylococcus) [Proceedings of Symposium on Mastitis Control, Espoo, Finland, June 1986, pages 10 to 12, Ed. Markus Sandholm; Belák-Tuboly and Varga: Állatorvosi mikrobiológia ("Veterinary Microbiology"; in Hungarian), Budapest, Mezőgazdasági Könyvkiadó, 1983; Mészáros and Szent-Iványi: Háziállatok fertőző betegségei ("Infective Diseases of Domestic Animals"; in Hungarian), Mezogazdasági Kiadó, 1985; Goodman-Gilman's: The Pharmacological Basis of Therapeutics, 7th Edition, MacMillan Publishing Co. Inc., New York, 1985; M. Jones, H. Nicholas Booth and L. E. McDonald: Veterinary Pharmacology and Therapeutics, 4th Edition, Iowa State University Press, USA].

Summing up, it can be stated that about 30 to 50% of the pathogens inducing the inflammation are only sensitive to the known compositions used for treating mastitis and metritis of cattle and these compositions do not possess any fungicidal effect at all. The majority of the known compositions is being used for decades whereby a resistance rapidly develops.

The aim of the present invention is to provide a novel broad-spectrum veterinary composition which is effective also in low doses and acts on both bacteria and fungi.

It has been found that the above aim can entirely be achieved by using polymyxin B or a pharmaceutically acceptable acid addition salt such as the sulfate or chloride thereof together with 1-(2-chlorophenyl)-diphenylmethyl-1H-imidazole (clotrimazole) or with 2-methyl-5,7-dichloro-8-hydroxyquinoline (chlorquinaldol), respectively.

The invention is based on the recognition that polymyxin B and clotrimazole or polymyxin B and chlorquinaldol, respectively are capable to significantly potentiate the antibacterial and fungicidal effect of each other.

Thus, the present invention relates to a novel, synergistically active veterinary composition, useful particularly for the treatment of mastitis and metritis, which comprises, based on 1 part by weight of polymyxin B or a pharmaceutically acceptable acid addition salt thereof, 1 to 1000 parts by weight of 1-(2-chlorophenyl)-diphenylmethyl-1H-imidazole (clotrimazole) or 1 to 400 parts by weight of 2-methyl-5,7-dichloro-8-hydroxyquinoline (chlorquinaldol), respectively optionally in admixture with carriers and/or additives commonly used in the pharmaceutical industry.

The effect of the compositions of the invention is supported by the following in vitro results.

The minimum inhibitory concentrations (MIC values) of the above compounds and their two-component combinations of 1:1 ratio by weight against the following microorganisms arising from mastitis and metritis processes of cattle were tested by using the serial dilution method in a phenol red-glucose broth medium (manufactured by DIFCO) or, by using a Sabouraud's broth medium, respectively in the cases of fungal strains.

A—*Staphylococcus aureus*
B—*Streptococcus zooepidermicus*
C—*Escherichia coli* 494
D—*Escherichia coli* 17
E—*Klebsiella pneumoniae*
F—*Pseudomonas aeruginosa*

G—*Candida albicans*
H—*Streptococcus agalactiae*
I—*Streptococcus dysgalactiae*
J—*Streptococcus uberis*
K—*Streptococcus faecalis*
L—*Listeria monocytogenes*
M—*Corynebacterium pyogenes*
N—*Salmonella typhimurium*
O—*Campylobacter fetus*
P—*Campylobacter jejuni*
R—*Bacteroides fragilis*
S—*Fusobacterium necrophorum*
T—*Mycoplasma bovis*
U—*Mycoplasma bovirhinis*
V—*Mycoplasma canadense*
Z—*Aspergillus fumigatus.*

Campylobacter strains were tested in a semiliquid thiol culture medium (manufactured by DIFCO). *Bacteroides fragilis* and *Fusobacterium necrophorum* strains were examined by using the agar dilution method on bloody agar containing also tryptose.

Bacterial strains were cultivated at 37° C. whilst the fungal strain (*Candida albicans*) was propagated at 26° C. The minimum inhibitory concentrations (MIC values) showing a bactericidal effect, i.e. complete inhibition of the growth of microorganisms whereby the media inoculated remained sterile, are summarized in Table 1.

ence of 0.25 μg/ml of polymyxin B together with 0.25 μg/ml of clotrimazole or chlorquinaldol, respectively is sufficient to kill the *Candida albicans* strain tested.

It can unequivocally be concluded from Table 1 that all tested microorganisms are inhibited even by a very low concentration of polymyxin B combined with clotrimazole or chlorquinaldol, respectively thus the danger of development of a resistance is also lowered.

According to the process of the invention, 1 part by weight of polymyxin B or its pharmaceutically acceptable acid addition salt is mixed with 1 to 1000 parts by weight of clotrimazole or 1 to 400 parts by weight of chlorquinaldol, respectively and with carriers and/or additives commonly used in the pharmaceutical industry and the mixture thus-obtained is converted into a pharmaceutical composition by a method known per se.

According to a preferred embodiment of the invention, the composition comprises, based on 1 part by weight of polymyxin B, 5 to 50 parts by weight of clotrimazole or chlorquinaldol, respectively in admixture with carriers and/or additives commonly used in the pharmaceutical industry.

The active ingredients are preferably converted into veterinary compositions that are suitable to treat mastitis and metritis such as suspensions, aerosols, uterine tablets (uterine rods), uterine capsules, foams and the like. These compositions usually contain the active ingredients in a total amount of 0.01 to 90% by weight,

TABLE 1

| Test substance | MIC values in μg/ml for the microorganisms | | | | | | |
|---|---|---|---|---|---|---|---|
| | A | B | C | D | E | F | G |
| Polymyxin B | 50 | 5 | 0.5 | 0.5 | 5 | 0.5 | 200 |
| Clotrimazole | 0.5 | 0.5 | >200 | >200 | >200 | >200 | 5 |
| Chlorquinaldol | 5 | 0.5 | 5 | 5 | 200 | 200 | 1 |
| 1:1 mixture by weight of polymyxin B with clotrimazole | 0.2 | 0.3 | 0.3 | 0.2 | 2 | 0.2 | 0.5 |
| 1:1 mixture by weight of polymyxin B with chlorquinaldol | 0.5 | 0.2 | 0.2 | 0.2 | 0.5 | 0.3 | 0.5 |

| | MIC values in μg/ml for the microorganisms | | | | | | |
|---|---|---|---|---|---|---|---|
| | H | I | J | K | L | M | N | O |
| Polymyxin B | 5 | 5 | 10 | 200 | 5 | 200 | 1 | 0.5 |
| Clotrimazole | 5 | 0.5 | 0.5 | 5 | 5 | 25 | 200 | 100 |
| Chlorquinaldol | 0.5 | 0.5 | 0.5 | 5 | 1 | 5 | 200 | 10 |
| Polymyxin B + clotrimazole | 1 | 0.2 | 0.1 | 1 | 1 | 5 | 0.5 | 0.2 |
| Polymyxin B + chlorquinaldol | 0.1 | 0.1 | 0.1 | 2 | 0.5 | 1 | 0.5 | 0.3 |

| | MIC values in μg/ml for the microorganisms | | | | | |
|---|---|---|---|---|---|---|
| | P | R | S | T | U | V | Z |
| Polymyxin B | 5 | 200 | 200 | 32 | 32 | 32 | 200 |
| Clotrimazole | 100 | 200 | 100 | 32 | 32 | 32 | 1 |
| Chlorquinaldol | 5 | 1.5 | 3 | 32 | 4 | 8 | 25 |
| Polymyxin B + clotrimazole | 1 | 20 | 15 | 10 | 10 | 15 | 0.5 |
| Polymyxin B + chlorquinaldol | 1 | 0.8 | 1 | 10 | 2 | 5 | 10 |

It is obvious from the data of Table 1 that e.g. *Staphylococcus aureus* is inhibited only by a high concentration (50 μg/ml) of polymyxin B but the common presence of 0.1 μg/ml of polymyxin B together with 0.1 μg/ml of clotrimazole is sufficient to ensure the bactericidal effect. *Escherichia coli* strains are inhibited by a low concentration (0.5 μg/ml) of polymyxin B alone, however, a lower concentration of 0.15 or 0.1 μg/ml of polymyxin B is also sufficient in the presence of clotrimazole. Clotrimazole alone has a very weak effect on these bacterial strains. The same observations can be registered in the common presence of polymyxin B and chlorquinaldol.

It bears a great importance that poymyxin B has practically no fungicidal action but the common prespreferably 0.1 to 10% by weight, suitably 0.1 to 2.0% by weight.

The veterinary compositions can be prepared by the means of carriers and auxiliary agents commonly used in the pharmaceutical industry, by employing pharmaceutical formulating processes known per se (see e.g.: Remington's Pharmaceutical Sciences, 16th Edition, Mack Publishing Co., Easton, USA, 1980). Suitable carriers and additives are fatty acid esters and ethers of fatty alcohols; emulsifying agents; colloidal silicon dioxide; tabletting auxiliary materials such as lactose, polyvinylpyrrolidone, talc, magnesium stearate and the like; stabilizing agents and the like; as stabilizing agent 1,1,1-trichloro-2-methylpropan-2-ol is preferably used in an amount of 0.1 to 10% by weight, suitably 0.5 to 2% by weight.

The veterinary compositions according to the invention are useful for the efficient treatment of mastitis and metritis as well as for combatting the simultaneously frequently occurring fungal infections.

The invention is illustrated in detail by the aid of the following non-limiting Examples.

EXAMPLE 1

Preparation of a Suspension

| Components | g |
|---|---|
| Polymyxin B | 0.01 |
| Clotrimazole | 0.10 |
| Softigen 701 (partial glyceride of unsaturated hydroxy fatty acid, manufactured by Dynamit Nobel Co.) | 0.20 |
| 1,1,1-Trichloro-2-methylpropan-2-ol | 0.05 |
| Colloidal silicon dioxide (with a specific surface of 200 m$^2$/g) | 0.24 |
| Mygliol 812 (triglyceride of C$_{8-12}$ saturated fatty acids, manufactured by Dynamit Nobel Co.) | 9.40 |
| | 10.00 |

After dissolving Softigen 701 in Mygliol 812, the other components are dispersed therein. (Before dispersing, the solid particles are crushed e.g. in an air jet mill to less than 10 μm size.) The suspension obtained is filled into a plastic udder syringe and used for the treatment of mastitis.

EXAMPLE 2

Preparation of a Suspension

| Components | g |
|---|---|
| Polymyxin B | 0.01 |
| Chlorquinaldol | 1.00 |
| Softigen 701 | 0.20 |
| 1,1,1-Trichloro-2-methylpropan-2-ol | 0.05 |
| Colloidal silicon dioxide | 0.24 |
| Mygliol 812 | 8.50 |
| | 10.00 |

The process described in Example 1 is followed to obtain a composition which is useful for the treatment of mastitis.

EXAMPLE 3

Preparation of a Suspension

| Components | g |
|---|---|
| Polymyxin B | 0.01 |
| Clotrimazole | 0.10 |
| Cremophor A 6 (ether formed from saturated fatty alcohols with ethylene oxide containing 6 ethoxy groups each in 1 molecule; manufactured by BASF) | 0.15 |
| Cremophor A 25 (ether formed from saturated fatty alcohols with ethylene oxide containing 25 ethoxy groups each in 1 molecule; manufactured by BASF) | 0.15 |
| 1,1,1-Trichloro-2-methylpropan-2-ol | 0.05 |
| Isopropyl myristate | 5.00 |
| Glyceryl monostearate | 0.14 |
| Cetyl stearyl 2-ethylhexanoate | 4.40 |
| | 10.00 |

Glyceryl monostearate and the Cremophor emulsifying agents are dissolved in the mixture of isopropyl myristate and cetyl stearyl 2-ethylhexanoate, then the solid particles are dispersed in the solution. The suspension thus obtained is used for the treatment of mastitis.

EXAMPLE 4

Preparation of a Suspension

| Components | g |
|---|---|
| Polymyxin B | 0.01 |
| Clotrimazole | 0.10 |
| Polyethylene glycol (molecular weight 25000) | 0.34 |
| 1,1,1-Trichloro-2-methylpropan-2-ol | 0.05 |
| Propylene glycol | 10.00 |
| Glyceryl caprylate | 10.00 |
| Mygliol 812 | 9.00 |
| Ether of nonylphenol with polyethylene glycol | 0.50 |
| | 30.00 |

Polyethylene glycol, nonylphenol polyethylene glycol ether and Mygliol 812 are added to the mixture of propylene glycol and glyceryl caprylate and the solid particles previously crushed to less than 10 μm size are suspended in the solution. The suspension obtained is filled into a plastic bottle and used for the treatment of metritis, e.g. by introducing it to the uterus through an uterine catheter.

EXAMPLE 5

Preparation of an Uterine Rod (Uterine Tablet)

| Components | g |
|---|---|
| Polymyxin B | 0.01 |
| Clotrimazole | 0.10 |
| Sodium lauryl sulfate | 1.10 |
| Anhydrous citric acid | 1.18 |
| Sodium hydrogen carbonate | 1.82 |
| Lactose | 3.00 |
| 1,1,1-Trichloro-2-methylpropan-2-ol | 0.05 |
| Polyvinylpyrrolidone | 0.30 |
| Talc | 0.20 |
| Magnesium stearate | 0.20 |
| Colloidal silicon dioxide (with a specific surface of 200 m$^2$/g) | 0.04 |
| | 7.00 |

The anhydrous citric acid having a particle size less than 200 μm, sodium hydrogen carbonate and polyvinylpyrrolidone are stirred while adding water in a vortex-flow granulating device for 6 minutes. The wet granulate is dried at 70° to 80° C., then the dry granulate is broken through a sieve of 1.0 mm thread-distance. The other components are added and the mixture obtained is transformed to uterine rods weighing 7.0 g each by using a press die of 60 mm in length and 10 mm in width in an eccentric tabletting machine. The uterine rod obtained is used for the treatment of metritis.

EXAMPLE 6

The process described in Example 5 is followed, except that 2.00 g of clotrimazole and 1.10 g of lactose are used.

EXAMPLE 7

The process described in Example 5 is followed, except that 0.01 g of clotrimazole and 3.0 g of lactose are used.

EXAMPLE 8

The process described in Example 5 is followed, except that 0.01 g of chlorquinaldol instead of clotrimazole and 3.09 of lactose are used.

EXAMPLE 9

Preparation of an Uterine Rod (Tablet)

| Components | g |
|---|---|
| Polymyxin B | 0.05 |
| Clotrimazole | 0.10 |
| Sodium dioctyl sulfosuccinate | 0.10 |
| Adipic acid | 1.40 |
| Sodium hydrogen carbonate | 1.10 |
| 1,1,1-Trichloro-2-methylpropan-2-ol | 0.05 |
| Lactose | 3.50 |
| Polyvinylpyrrolidone | 0.30 |
| Talc | 0.20 |
| Magnesium stearate | 0.24 |
| | 7.00 |

The solution of polyvinylpyrrolidone and sodium dioctyl sulfosuccinate in 100 ml of ethanol is added to the mixture of adipic acid having a particle size less than 200 μm, sodium hydrogen carbonate and lactose while stirring in a vortex-flow apparatus. After granulating for 6 minutes the granulate is dried, then broken through a sieve of 1.0 mm thread-distance, the other components are added and the mixture obtained is transformed to uterine rods as described in Example 5.

EXAMPLE 10

The process described in Example 9 is followed, except that chlorquinaldol is used instead of clotrimazole.

We claim:

1. A synergistic veterinary composition useful for treating mastitis and related fungal infections which comprises: a suitable carrier and as an active agent a pharmaceutically effective amount of a combination of 1) 6,9,18-tris(2-aminoethyl)-15-benzyl-21-[2,8-bis(2-aminoethyl)-5-(1-hydroxyethyl)-15-methyl-4,7,10-trioxo-3,6,9-triazaheptadecanaminoamino]-3-(1-hydroxyethyl)-12-isobutyl-1,4,7,10,13,16,19-heptaazacyclotricosane-2,5,8,11,14-14,17,20-heptaone or a pharmaceutically acceptable salt thereof and 2) 2-methyl-5,7-dichloro-8-hydroxyquinoline, wherein the ratio of the two components is about 1:1.

2. A process for treating bovine mastitis and metritis and related fungal infections which comprises administering to the animal in need thereof a pharmaceutically effective amount of the synergistic veterinary composition of claim 1.

* * * * *